United States Patent
Moreau

(10) Patent No.: US 12,350,228 B2
(45) Date of Patent: Jul. 8, 2025

(54) SYSTEM AND DEVICE FOR IRRIGATING AND CLEANING NASAL CAVITIES

(71) Applicant: Dany Moreau, Trois-Rivieres (CA)

(72) Inventor: Dany Moreau, Trois-Rivieres (CA)

(*) Notice: Subject to any disclaimer, the term of this patent is extended or adjusted under 35 U.S.C. 154(b) by 963 days.

(21) Appl. No.: 17/313,827

(22) Filed: May 6, 2021

(65) Prior Publication Data

US 2022/0354741 A1   Nov. 10, 2022

(51) Int. Cl.
| | |
|---|---|
| *A61H 35/04* | (2006.01) |
| *A61M 1/00* | (2006.01) |
| *A61M 3/02* | (2006.01) |

(52) U.S. Cl.
CPC ............... *A61H 35/04* (2013.01); *A61M 1/70* (2021.05); *A61M 3/0279* (2013.01); *A61H 2201/1607* (2013.01); *A61M 2210/0618* (2013.01)

(58) Field of Classification Search
CPC ............ A61H 35/04; A61H 2201/1607; A61H 2201/5051; A61H 2203/0456; A61M 1/70; A61M 3/0279; A61M 3/0241; A61M 3/0287; A61M 3/0283; A61M 16/06; A61M 16/208; A61M 25/02; A61M 2025/022; A61M 2025/0226; A61M 2025/0246; A61M 2025/028
USPC .......................................... 604/303, 174–180
See application file for complete search history.

(56) References Cited

U.S. PATENT DOCUMENTS

| | | | |
|---|---|---|---|
| 1,502,163 A | 7/1924 | Sprague | |
| 2,078,180 A | 4/1937 | Kronenberg | |
| 3,088,459 A * | 5/1963 | Rabinoff | A61H 35/008 4/615 |
| 4,333,451 A | 6/1982 | Palschs | |
| 9,730,858 B2 | 8/2017 | Naoum | |
| 2002/0099331 A1* | 7/2002 | Burchfield | A61M 3/0241 604/94.01 |
| 2008/0047559 A1 | 2/2008 | Fiori | |
| 2010/0152653 A1 | 6/2010 | Hoke et al. | |
| 2012/0055478 A1* | 3/2012 | Wilkinson | A61M 16/0051 128/204.23 |
| 2013/0012869 A1* | 1/2013 | Cha | A61M 3/0258 604/28 |
| 2014/0345607 A1* | 11/2014 | Skov | A62B 7/10 128/202.22 |
| 2015/0224246 A1 | 8/2015 | Layer et al. | |
| 2018/0207332 A1* | 7/2018 | Reever | A61M 1/743 |
| 2019/0232031 A1* | 8/2019 | Siegel | A61H 35/04 |

* cited by examiner

*Primary Examiner* — Nathan R Price
*Assistant Examiner* — John A Doubrava

(57) ABSTRACT

A system for irrigating and cleaning nasal cavities is provided. In some embodiments, the system includes a stand configured to hold an aqueous solution container. A primary incoming tube leading to a face mask device configured to be worn by a user. In one embodiment, the solution is gravity fed directed through the primary incoming tube into at least one port of the face mask device. A drain line leads from the face mask device to a collection container.

9 Claims, 3 Drawing Sheets

SYSTEM AND DEVICE FOR IRRIGATING AND CLEANING NASAL CAVITIES

CROSS-REFERENCE TO RELATED APPLICATIONS

The present application claims priority to UK request number GB2019732.3, filed on Dec. 14, 2020, the disclosure of which is hereby incorporated in its entirety at least by reference.

BACKGROUND OF THE INVENTION

1. Field of the Invention

The present invention relates generally to respiratory equipment but more particularly to a system and device for irrigating and cleaning nasal cavities.

2. Description of Related Art

The use of nasal irrigation, like neti pots and similar devices for pouring saline water into the nose and through the sinuses has been known for centuries. The benefits of doing so has also been studied for some time now and is gaining in popularity among people interested in alternative medicine. More recently, this nasal irrigation technique has even been accepted as effective by western medicine as a way to prevent or treat symptoms of allergies, colds, and nasal congestion. There are even studies suggesting that various medications can be used when performing irrigation to treat various diseases. Although relatively simple to perform, nasal irrigation and cleaning does require a little getting used to and may not always be performed in the best way. They are designed to be used while standing up, which limits their efficiency. There is a need for a better way of performing that task. Consequently, a system and device for irrigating and cleaning nasal cavities is provided.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is a main object of the present invention to provide for a device for using proven scientific processes for irrigating and cleaning nasal cavities by allowing liquid to go deep into the sinuses cavities by immersing them, while the user is lying down. It is another object of the present invention to confine the solution used and the liquid discharges which result therefrom by way of confinement in the watertight face mask and the conduits towards the collection container. It is yet another object of the present invention, to enhance the experience during a treatment.

In order to do so, a face mask device for irrigating and cleaning nasal cavities is provided, the face mask comprising an incoming supply port configured to receive an incoming supply tube configured to flow aqueous solution through the incoming supply port; a pair of supply tubes connected to the incoming supply port, wherein the pair of supply tubes lead into a pair of nostrils of a user; a pair of drain tubes leading from the pair of nostrils to an outlet positioned on the facemask; and, a three way valve positioned to control the flow through the incoming supply port and to direct the flow to a supply tube of the pair of supply tubes such that flow of aqueous solution is enabled to be directed to a nostril of the pair of nostrils.

In one embodiment, a pair of holding baskets is provided, wherein the pair of supply tubes feed into the pair of holding baskets, wherein each holding basket of the pair of holding baskets are configured to be positioned in each nostril of the user. In one embodiment, the pair of drain tubes are connected to the pair of holding baskets. In another embodiment, each holding basket is configured to bring in the aqueous solution into a nasal cavity of the pair of nostrils while letting out excretion flow to the pair of drain tubes from each holding basket. In yet another embodiment, the pair of drain tubes are shaped and configured to pass around a mouth of the user. In one embodiment, a sleeve is positioned at a bottom portion of the face mask, such that the pair of drain tubes pass through the sleeve to the outlet. In one embodiment, the sleeve includes at least one passageway enabling excretions evacuation coming from a mouth of the user. In another embodiment, a threaded ring configured to receive and connect a drain line to the outlet is provided. In yet another embodiment, head straps configured to secure the face mask to the user during use are provided.

In another aspect of the invention the face mask is watertight to allow for full immersion of nasal cavities while allowing for circulation of fresh air by way of at least one air outlet valve and at least one air inlet valve.

In another aspect of the invention, a system for irrigating and cleaning nasal cavities of a user is provided, comprising a stand configured to hold an aqueous solution container; a primary incoming tube connected to the aqueous solution container; a face mask device comprising: an incoming supply port configured to receive the primary incoming supply tube; a pair of supply tubes connected to the incoming supply port, wherein the pair of supply tubes lead into a pair of nostrils of the user; a pair of drain tubes leading from the pair of nostrils to an outlet positioned on the facemask; and, a three way valve positioned to control the flow through the incoming supply port and to direct the flow to a supply tube of the pair of supply tubes such that flow of aqueous solution is enabled to be directed to a nostril of the pair of nostrils; a drain line connected to the outlet in fluid communication with the pair of drain tubes; and, a collection container configured to receive the waste from the drain line.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a system and device for irrigating and cleaning nasal cavities.

Figure 1:
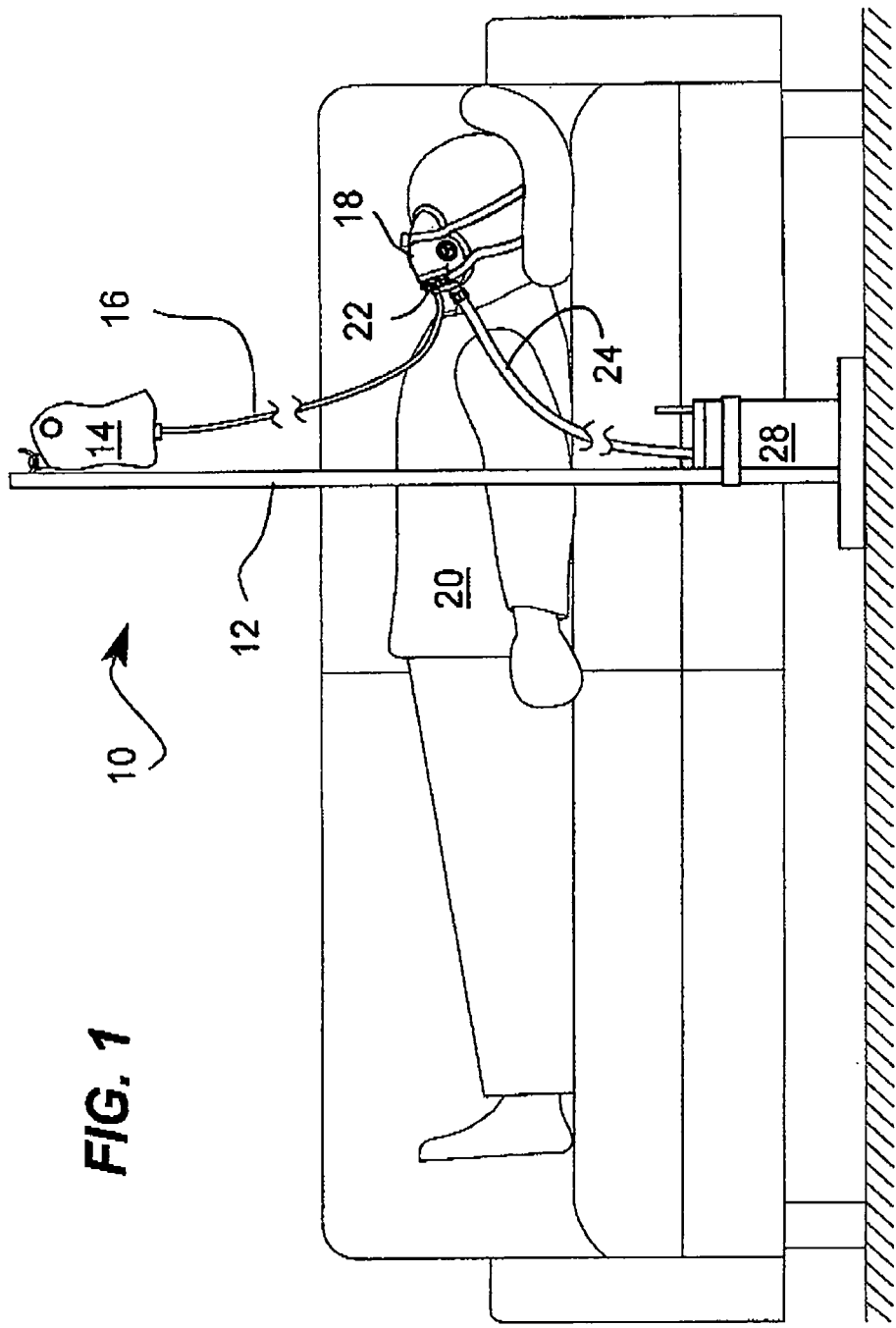
FIG. 1 illustrates a system for irrigating and cleaning nasal cavities in use according to an embodiment of the present invention.
Figure 2:
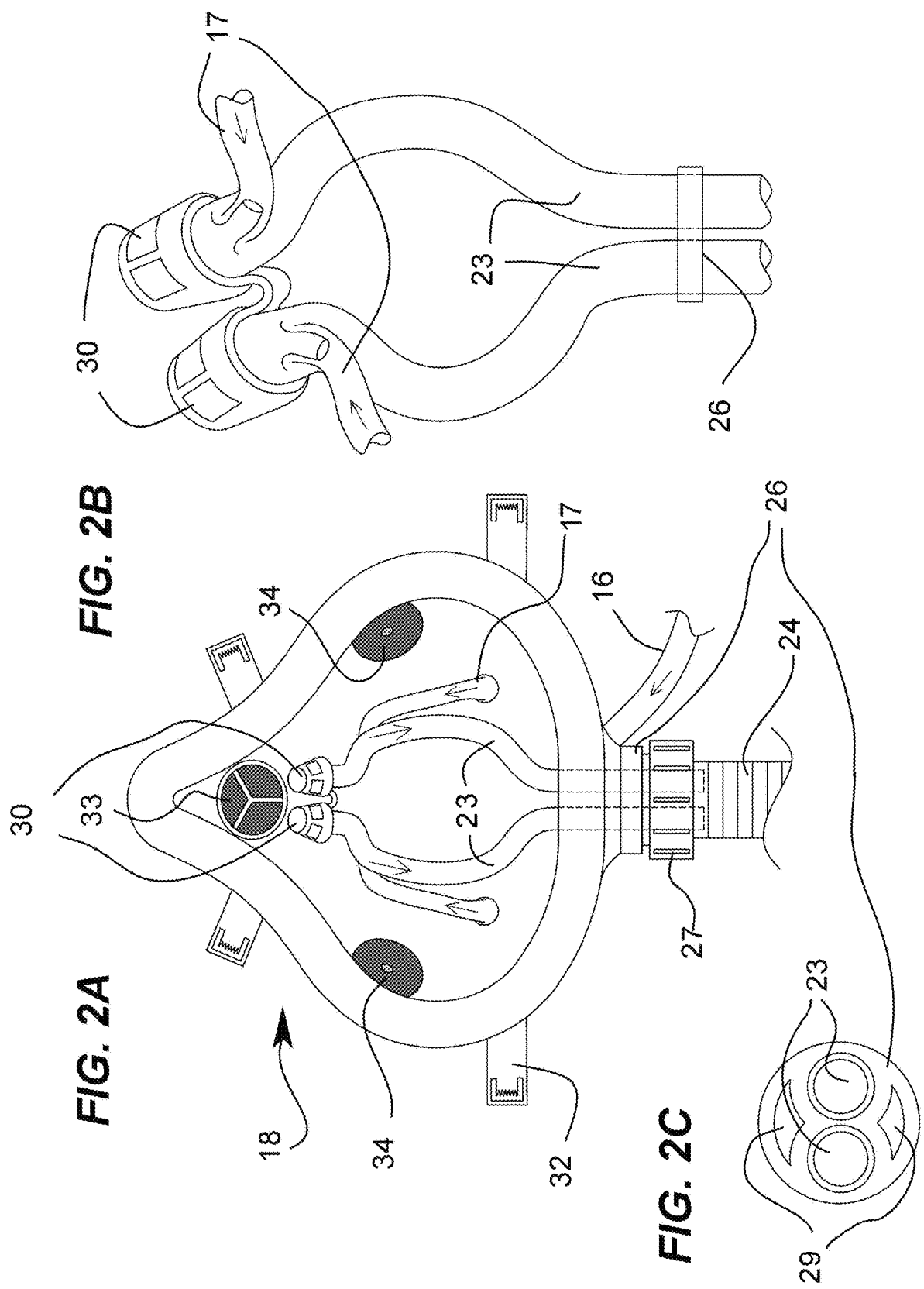
FIG. 2A is a rear view of the mask component of the device according to an embodiment of the present invention.
FIG. 2B is a detail view of the tubes and baskets according to an embodiment of the present invention.
FIG. 2C is a top view of the drain tubes according to an embodiment of the present invention.
Figure 3:
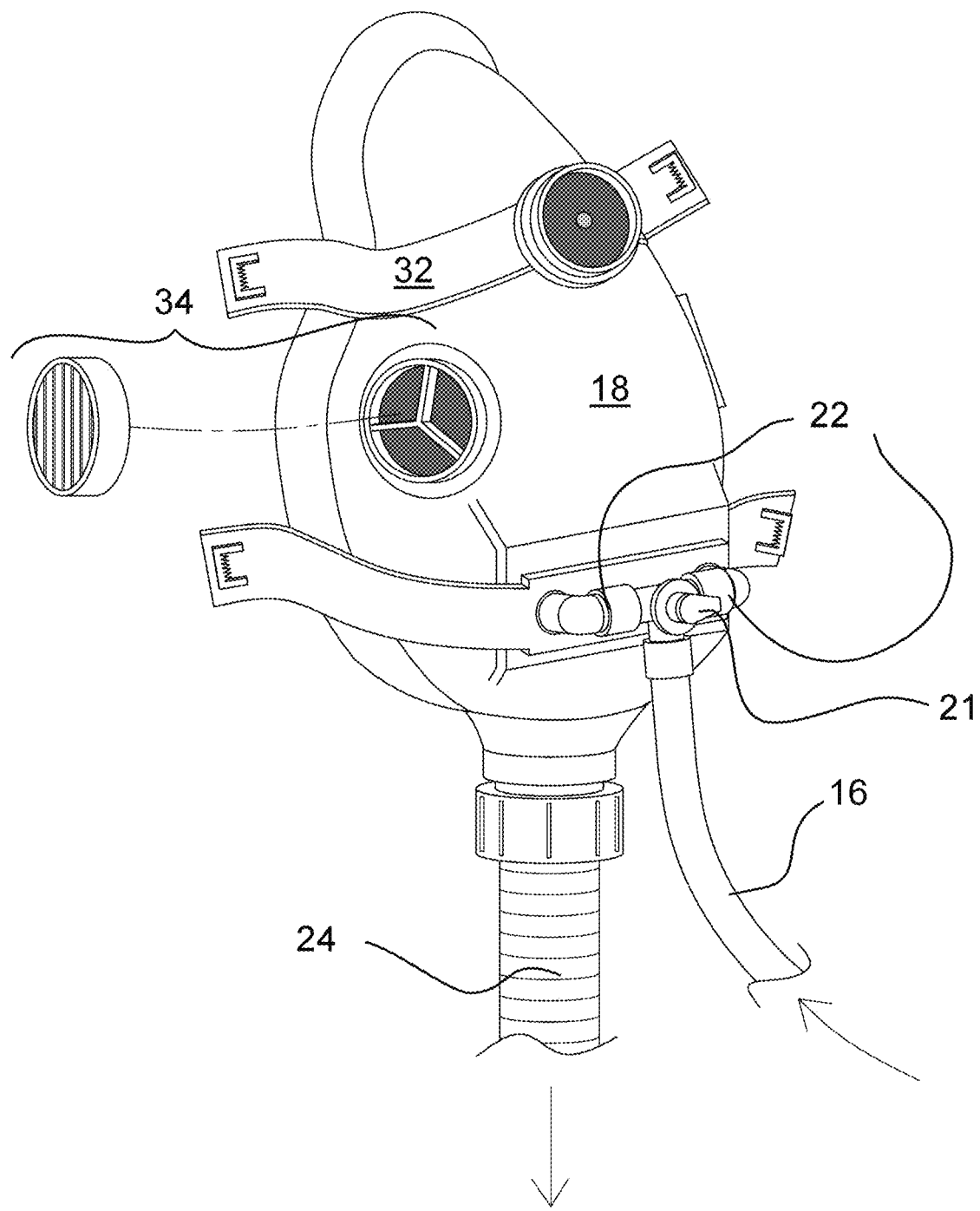
FIG. 3 is an isometric view of the mask according to an embodiment of the present invention.

Referring now to FIG. 1, a system 10 for irrigating and cleaning nasal cavities in use is shown according to an embodiment of the present invention. In some embodiments, the system comprises a stand 12 configured to hold an aqueous solution container 14. The system further comprises a primary incoming tube 16 leading to a water tight face mask device 18 configured to be worn by a user 20. In one embodiment, the solution is gravity fed directed through the primary incoming tube into at least one port 22 of the face mask 18. A drain line 24 leads from the face mask 18 to a collection container 28. Further details of the device and use will be described in greater detail below.

Referring now to FIGS. 2A-C and FIG. 3, the face mask device 18 comprises a three way valve 21 to control flow from the primary incoming tube 16 through the at least one port 22. In some embodiments, two ports are provided to direct a pair of secondary incoming tubes 17 to each nostril of the user. More specifically, the pair of secondary incoming tubes 17 feed into a pair of holding baskets 30, one for each nostril, wherein each holding basket is configured to bring in the solution into the nasal passages while letting out the excretion flow to a pair of drain tubes 23 from each holding basket 30. The pair of drain tubes 23 functioning as outlets for the waste, wherein the pair of drain tubes lead to drain line 24.

Advantageously, the drain tubes 23 are shaped and configured to pass around the mouth of the intended user. In some embodiments, a sleeve 26 is provided at a bottom portion of the face mask 18, such that the drain tubes pass through the sleeve 26. Further, in some embodiments, the sleeve 26 contains two additional passageways 29 for possible excretions evacuation coming from the mouth enabling these excretions to be evacuated towards and into the drain line 24. In one embodiment, the drain line 24 is secured to the face mask 18 via a threaded ring 27.

In some embodiments, the face mask 18 further comprises at least one head strap 32 for securing the face mask 18 to the user during use. In some embodiments, at least one air outlet valve 33 and at least one air inlet valve 34 is provided for the circulation of fresh air. In some embodiments, a means for retaining and keeping proper alignment between the drain tubes 23 and the drain line 24 is provided, which allows for the proper placement and angle of the holding baskets 30 as well. In some embodiments, the retaining means is the sleeve 26 as previously discussed or a collar.

In use, the user 20 is instructed to place the three way valve 21 in the closed position, put the aqueous solution in the solution container 14, and install the container on the stand 12. Next, the user is instructed to secure the face mask device 18 to their face and lie down on a bed or couch. The user then selects, by way of the three way valve 21, towards which nostril is desired to receive the incoming solution via the primary incoming tube 16, wherein the solution travels through the incoming tube 16, then into the face mask device 18 and through a secondary incoming tube 17 via port 22 to the desired nostril and nasal cavity. Then, out drain tube 23 to the drain line 24, and into the collection container 28. The solution can go from the right nostril into the left nostril or vice versa. The nasal cavities are immersed for the time required for the treatment so that the active ingredients can take effect. Usually, the solution does not travel down to the throat unless the user 20 has a malformation of the mouth or palate. In order to completely drain the solution, the user 20 needs to stand up, or at least turn his head sideways and blow through his nose.

Although the invention has been described in considerable detail in language specific to structural features, it is to be understood that the invention defined in the appended claims is not necessarily limited to the specific features described. Rather, the specific features are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) are not used to show a serial or numerical limitation but instead are used to distinguish or identify the various members of the group.

What is claimed is:

1. A face mask device for irrigating and cleaning nasal cavities of a user, the face mask comprising:
   an incoming supply port configured to receive an incoming supply tube configured to flow aqueous solution through the incoming supply port;
   a pair of supply tubes connected to the incoming supply port;
   a pair of holding baskets, wherein the pair of supply tubes feed into the pair of holding baskets, wherein the pair of holding baskets are configured to be positioned into the user's nostrils;

a pair of drain tubes connected to the pair of holding baskets, wherein the pair of drain tubes lead to a drain line;

a sleeve positioned at a bottom portion of the face mask, such that the pair of drain tubes pass through the sleeve to the drain line and the sleeve includes at least one passageway enabling excretions evacuation coming out from the user's mouth to be directed towards and into the drain line;

a three way valve positioned to control the flow through the incoming supply port and to direct the flow to a supply tube of the pair of supply tubes such that flow of aqueous solution is enabled to be directed to a desired nostril of the user's nostrils such that the three way valve is operable to alternate the flow of aqueous solution between the user's nostrils;

wherein each holding basket is configured to bring in the aqueous solution into a nasal cavity of the user's nostrils while letting out excretion flow to the pair of drain tubes from each holding basket, and the face mask configured for use by a user that is positioned in a lying down supine position.

2. The face mask of claim 1, the pair of drain tubes are shaped and configured to pass around the user's mouth.

3. The face mask of claim 1, further comprising a threaded ring configured to receive and connect the drain line.

4. The face mask of claim 1, further comprising head straps configured to secure the face mask to the user during use.

5. The face mask of claim 1, wherein the face mask is configured to make a water tight seal on the user's face during use enabling an immersion of the aqueous solution within the user's nasal cavities while allowing for circulation of fresh air by way of at least one air outlet valve and at least one air inlet valve.

6. A system for irrigating and cleaning nasal cavities of a user comprising:

a stand configured to hold an aqueous solution container having aqueous solution;

a primary incoming supply tube connected to the aqueous solution container;

a face mask device comprising:

an incoming supply port configured to receive the primary incoming supply tube;

a pair of supply tubes connected to the incoming supply port, wherein the pair of supply tubes lead into a pair of connecting baskets, the pair of connecting baskets configured for use in the user's nostrils;

a pair of drain tubes leading from the pair of connecting baskets to a drain line;

a sleeve positioned at a bottom portion of the face mask, such that the pair of drain tubes pass through the sleeve to the drain line and the sleeve includes at least one passageway enabling excretions evacuation coming out from the user's mouth to be directed towards and into the drain line;

a three way valve is positioned and configured to control a flow of aqueous solution through the incoming supply port and is configured to direct the flow of aqueous solution to a supply tube of the pair of supply tubes such that flow of aqueous solution is enabled to be directed to a desired nostril of the user's nostrils, such that the three way valve is operable to alternate the flow of aqueous solution between the user's nostrils;

wherein each holding basket is configured to bring in the aqueous solution into a nasal cavity of the user's nostrils while letting out excretion flow waste to the pair of drain tubes from each holding basket; and the face mask configured to immerse, irrigate and clean nasal cavities, and further configured for use by a user positioned in a lying down position;

and a collection container configured to receive the excretion flow waste from the drain line.

7. The face mask of claim 6, the pair of drain tubes are shaped and configured to pass around the user's mouth.

8. The face mask of claim 6, further comprising a threaded ring configured to receive and connect the drain line.

9. The face mask of claim 6, further comprising head straps configured to secure the face mask to the user during use.

* * * * *